US00PP35422P2

(12) United States Plant Patent
Kolster et al.

(10) Patent No.: US PP35,422 P2
(45) Date of Patent: Oct. 17, 2023

(54) ***HYDRANGEA* PLANT NAMED 'HOKOMAVERDE'**

(50) Latin Name: *Hydrangea macrophylla*
Varietal Denomination: Hokomaverde

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: KOLSTER HOLDING BV (50%), Boskoop (NL); HORTEVE BREEDING BV (50%), Aalsmeer (NL)

( * ) Notice: Subject to any disclaimer, the term of this patent is extended or adjusted under 35 U.S.C. 154(b) by 0 days.

(21) Appl. No.: 18/086,418

(22) Filed: Dec. 21, 2022

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea macrophylla* plant named 'Hokomaverde' that is characterized by its inflorescences with sterile flower sepals that are green and white in color, its mophead inflorescences that are large in size, and its suitability for use as a potted plant.

3 Drawing Sheets

Botanical classification: *Hydrangea macrophylla.*
Varietal denomination: 'Hokomaverde'.

BACKGROUND OF THE INVENTION

The present invention relates to a new and distinct cultivar of *Hydrangea macrophylla* and will be referred to hereafter by its cultivar name, 'Hokomaverde'. 'Hokomaverde' represents a new bigleaf *Hydrangea,* a perennial shrub grown for use in the landscape and as a potted plant.

'Hokomaverde' derived from an ongoing controlled breeding program directed by the Inventors. A goal of the breeding program was to develop a new cultivar of *Hydrangea* with white flowers that is suitable for use as a potted plant.

'Hokomaverde' arose from a controlled cross made by the Inventors in Boskoop, The Netherlands in May of 2010 between *Hydrangea* 'Renate 4x' (not patented) as the female parent and *Hydrangea* '08-012-03 (not patented) as the male parent. 'Hokomaverde' was selected as a single unique plant from amongst the resulting seedlings in May of 2012.

Asexual propagation of the new cultivar was first accomplished by stem cuttings by one of the Inventors in July of 2012 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomaverde' as a unique cultivar of *Hydrangea macrophylla.*

1. 'Hokomaverde' exhibits inflorescences with sterile flower sepals that are green and white in color.

2. 'Hokomaverde' exhibits mophead inflorescences that are large in size.
3. 'Hokomaverde' exhibits suitability for use as a potted plant.

The female parent of 'Hokomaverde' differs from 'Hokomaverde' in having leaves that are darker green in color and inflorescences with sterile flower sepals that are pink in color. The male parent of 'Hokomaverde' differs from 'Hokomaverde' in having mophead inflorescences that are more round in shape and all white in color. 'Hokomaverde' can be most closely compared to the *Hydrangea macrophylla* cultivars 'Hokomano' (U.S. Plant Pat. No. 22,696) and 'Hortmawin' (not patented). 'Hokomano' and 'Hortmawin' are both similar to 'Hokomaverde' in having inflorescences that are white and green in color and in being suitable for use as potted plants. 'Hokomano' differs from 'Hokomaverde' in having inflorescences with a more flattened shape and sterile flower sepals with more green coloring that is darker green in color. 'Hortmawin' differs from 'Hokomaverde' in having inflorescences with sterile flower sepals with lighter green coloration with red markings and margins that are more dentate.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plants Nouveau.

BRIEF DESCRIPTION OF THE DRAWINGS

The accompanying colored photographs illustrate the overall appearance and distinct characteristics of the new *Hydrangea.* The photographs were taken of a one-year-old plant of 'Hokomaverde' as grown in a greenhouse in a 4-inch container in Vineland, B.C., Canada.

The photograph in FIG. 1 provides a side view of 'Hokomaverde' in bloom.

Figure 1:
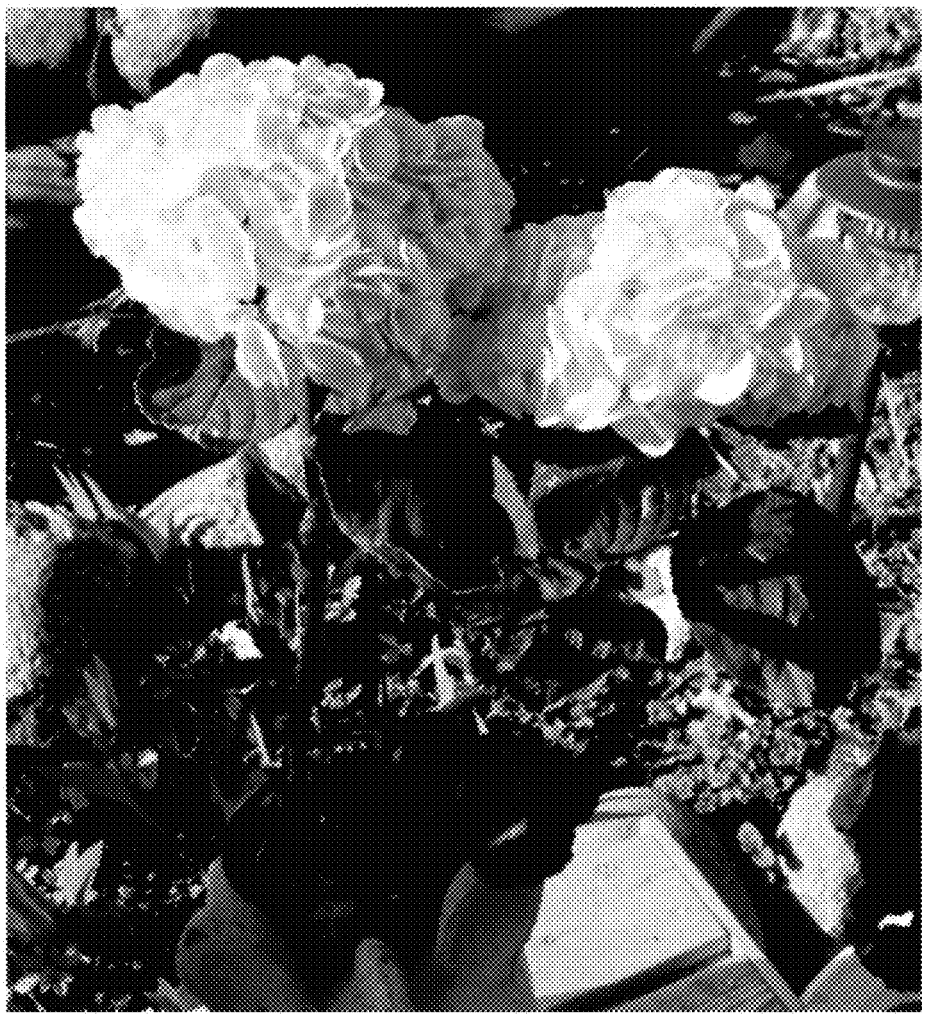
Figure 2:
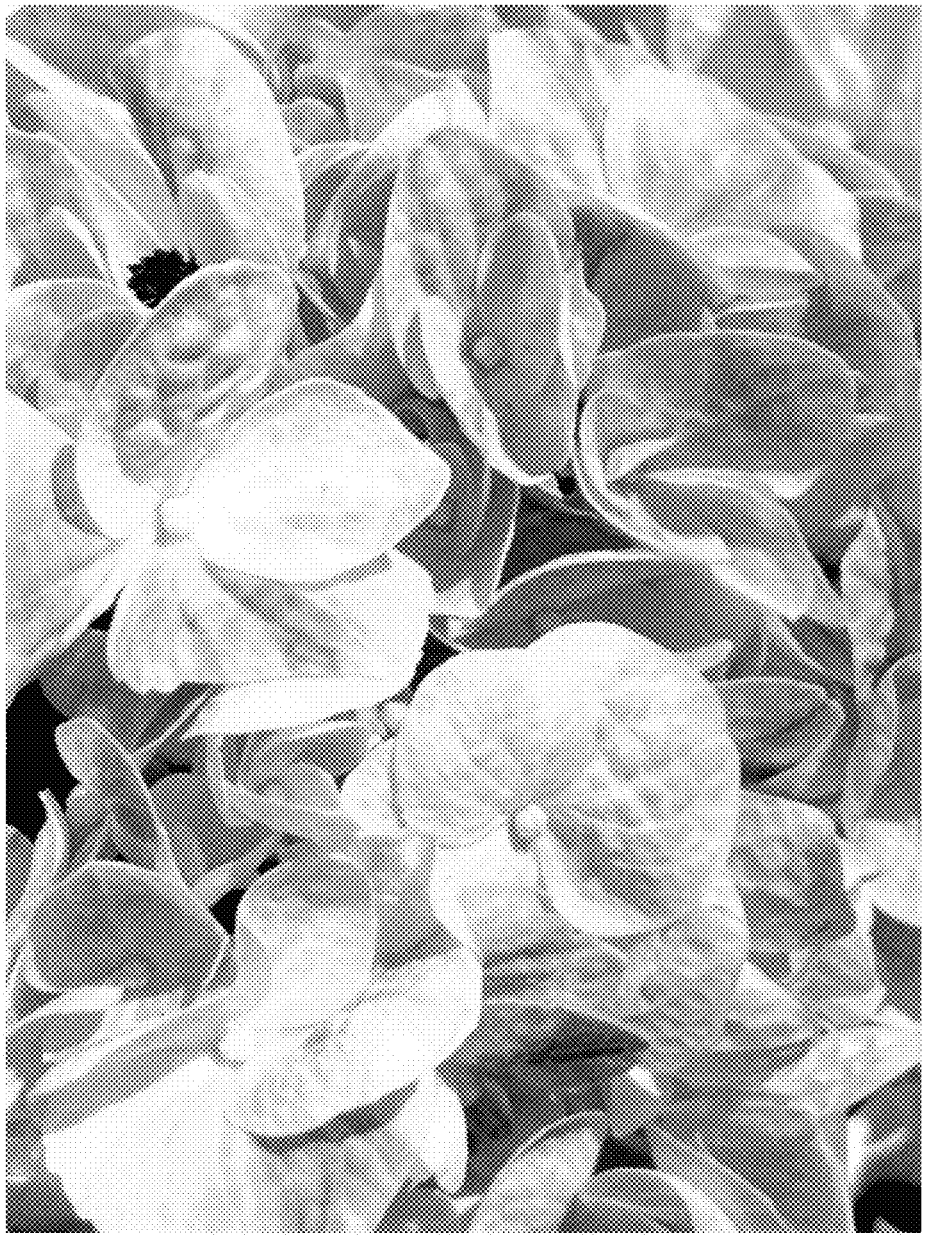

The photograph in FIG. 2 provides a close-up view of a fully open inflorescence of 'Hokomaverde'.

Figure 3:
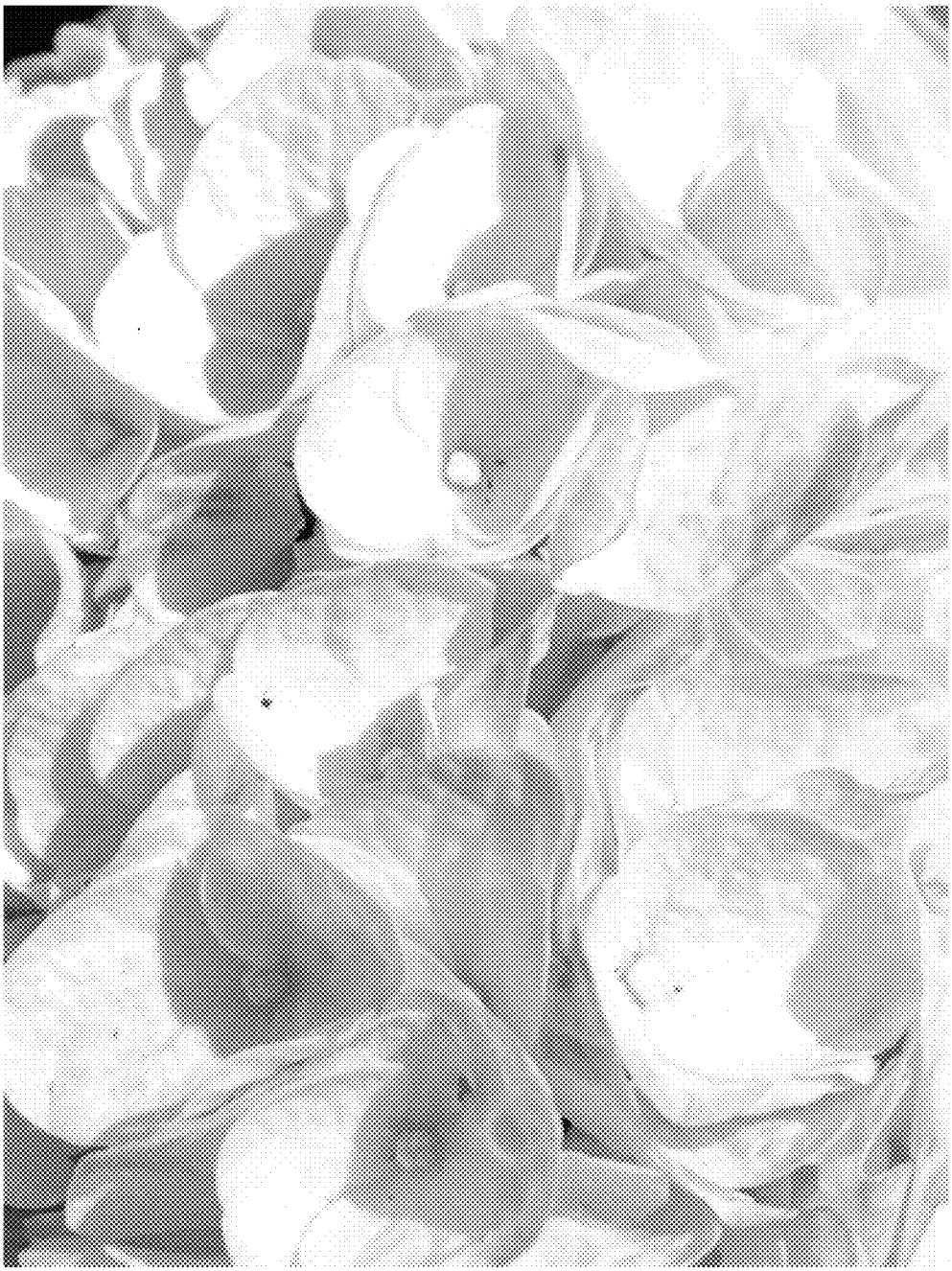

The photograph in FIG. 3 provides a close-up view of a maturing inflorescence of 'Hokomaverde'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of one-year-old plants of 'Hokomaverde' as grown in a greenhouse in 4-inch containers in Vineland, B.C., Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late spring to late summer with flowers showy at least for 2 months in The Netherlands.

*Plant type.*—Deciduous shrub, mophead type *Hydrangea.*

*Plant habit.*—Upright.

*Height and spread.*—An average of 37 cm in in height and 32 cm in spread as grown in a 4-inch container, reached 1 m in height and spread as a 3-year-old plant in the landscape.

*Hardiness.*—At least in U.S.D.A. Zones 5 to 9.

*Diseases and pests.*—No susceptibility and resistance to diseases or pests has been observed.

*Root description.*—Fine and fibrous, 161C in color.

*Propagation.*—Stem cuttings.

*Root development.*—An average of 6 weeks for root initiation with a young rooted plant produced in an average of 18 weeks.

*Growth rate and vigor.*—Moderate.

Branch description:

*Branch shape.*—Rounded.

*Branch strength.*—Strong.

*Branch color.*—Young; 144B, mature; 146B, old bark; N200A and N199B.

*Branch size.*—An average of 24 cm in length (excluding inflorescence) and 6 mm in diameter.

*Branch surface.*—Young branches slightly glossy, glabrous, older stems matte, glabrous, branches are moderately to densely covered with lenticels; linear and thin in shape, average of 35 per 1 cm diameter, average of 2 mm in length, 0.3 mm in width, 200A in color.

*Branch aspect.*—Held upright to slightly outward.

*Internode length.*—An average of 4 cm.

*Branching.*—Freely branching with an average of 3 lateral branches.

Foliage description:

*Leaf shape.*—Broad ovate.

*Leaf arrangement.*—Opposite.

*Leaf division.*—Simple.

*Leaf base.*—Short attenuate.

*Leaf apex.*—Short apiculate.

*Leaf margins.*—Coarsely serrate.

*Leaf venation.*—Pinnate, color; upper and lower surface 193A.

*Leaf size.*—Up to 11 cm in length and 8 cm in width.

*Leaf attachment.*—Petiolate.

*Leaf number.*—An average of 8 to 10 per lateral stem.

*Leaf surface.*—Upper surface; leathery appearance, matte and glabrous, lower surface matte and glabrous.

*Leaf color.*—Young foliage; upper surface 137A, lower surface 147B, mature foliage; upper surface 147A with an overlay of 203B, lower surface 147B.

*Petioles.*—An average of 2 cm in length and 3 mm in diameter, upper and lower surface color 144A, both surfaces are glabrous and glossy.

Inflorescence description:

*Inflorescence type.*—Terminal panicle, full flattened mophead in form, comprised of fertile flowers and single sterile flowers.

*Lastingness of inflorescence.*—Persistent for 3 months.

*Inflorescence number.*—One per lateral.

*Inflorescence size.*—Average of 11 cm in height, 19 cm in diameter.

*Flower number.*—Average of 150 sterile flowers and 16 fertile flowers per panicle.

*Flower fragrance.*—None.

*Flower aspect.*—Upright to outward.

*Flower size.*—Sterile flowers; an average of 2.7 cm in diameter, 1 cm in depth, fertile flowers; do not open.

*Flower type.*—Rotate.

*Flower buds.*—Sterile flowers; average of 3 mm in width and 4 mm in depth, obovate in shape, color when young; 145A, color when mature before dropping; NN155B, fertile flowers; average of 2 mm in width and 3 mm in depth, obovate in shape, color when young; 145A, color when mature before dropping; NN155B.

*Peduncles.*—Moderately strong, average of 3 cm in length and 3 mm in width, color; base to middle 144C, middle to top 145C, moderately covered with lenticels; linear and thin in shape, average of 10 per 1 cm diameter, average of 2 mm in length, 0.3 mm in width, 183A in color, surface is glossy and densely covered with very minute woolly hairs, NN155D in color, 0.2 mm in length.

*Pedicels.*—Moderately strong, up to 3 cm in length and 1 mm in width, color; NN155B to N155B, sometimes base is flushed with 145D, moderately covered with lenticels; linear and thin in shape, average of 8 per 1 cm diameter, average of 2 mm in length, 0.3 mm in width, 72B to 72C in color, surface is glossy and densely covered with very minute woolly hairs, NN155D in color, 0.2 mm in length.

*Petals.*—Sterile flowers; petals do not open, petal spot 2 mm in diameter and NN155C in color when mature, fertile flowers; petals do not open

*Sepals.*—Sterile flowers; showy, 4, deltoid to reniform in shape, moderately to strongly overlapping, rotate in arrangement, entire margins moderately undulate and dentated, apex is very slightly retuse to bluntly pointed, cuneate base, average of 1.5 cm in length and 2 cm in width, upper and lower surface glabrous and satiny, color: when opening upper and lower surface; NN155C, randomly mottled with N144A and 143A, when fully open upper and lower surface; NN155C, fertile flowers; do not open.

Reproductive organs:

*Presence.*—Not observed; fertile flowers drop after budding, gynoecium and androecium not developed.

*Fruit and seed.*—Not observed.

It is claimed:

1. A new and distinct cultivar of *Hydrangea* plant named 'Hokomaverde' substantially as herein illustrated and described.

* * * * *